United States Patent [19]

Widran et al.

[11] 4,061,135
[45] Dec. 6, 1977

[54] BINOCULAR ENDOSCOPE

[75] Inventors: Jerrold Widran, Glencoe; Stuart A. Solin, Chicago, both of Ill.

[73] Assignee: Jerrold Widran, Chicago, Ill.

[21] Appl. No.: 727,291

[22] Filed: Sept. 27, 1976

[51] Int. Cl.² ............................................. A61B 1/06
[52] U.S. Cl. ........................................ 128/6; 350/23; 350/36
[58] Field of Search ............... 128/3, 4, 6, 7, 8, 303.15; 350/23, 36, 130, 96 R

[56] References Cited

U.S. PATENT DOCUMENTS

| | | | |
|---|---|---|---|
| 815,657 | 3/1906 | Swasey | 350/23 |
| 3,186,300 | 6/1965 | Litimann | 128/3 |
| 3,520,587 | 7/1970 | Toshio Tasaki et al. | 350/36 |
| 3,796,220 | 3/1974 | Bredemeier | 350/36 |
| 3,850,162 | 11/1974 | Iglesias | 128/6 |

Primary Examiner—Robert W. Michell
Assistant Examiner—Henry S. Layton
Attorney, Agent, or Firm—Kegan, Kegan & Berkman

[57] ABSTRACT

A binocular endoscope for diagnostic work, medical treatment and surgical procedures providing depth perception in the image of an object viewed. Image transmittal from the viewed object to the viewing station is through a non-distorting, high resolution, optical system utilizing long path length lens means. Selectable field viewing through 360° of continuous rotation, with preservation with image conformity, is achieved through the use of a dove prism in combination with mechanical linkage to compensate for rotation effects. The apparatus also includes field illumination means, fluid input and exhaust channels and a manipulable surgical element.

25 Claims, 17 Drawing Figures

BINOCULAR ENDOSCOPE

BACKGROUND OF THE INVENTION

The present invention relates to a binocular endoscope or similar instrument finding utility in the examination and in the surgical treatment of the interior of a hollow organ, as, for example, the urethra and the bladder. More particularly, the invention is directed to an endoscope provided with a pair of coextensive optical systems for directing light through two parallel equivalent optical paths, thus providing depth perception in the image of an object or field viewed.

Binocular or stereoscopic endoscopes are known in the prior art. For example, stereoscopic endoscopes utilizing flexible fiber optical systems have been described, such a system being the subject of Tasaki et al U.S. Pat. No. 3,520,587. Also, various optical systems have been utilized for obtaining an upright image, one such technique resorting to the twisting of fibers through 180° and a second technique utilizing Porro prisms. In still other arrangements the optical fiber bundles or sheaths have been arranged to cross each other at their midpoints. However, the latter system results in an image inversion between raised and recessed portions. Focusing has been achieved through the use of auxiliary elements such as Amici prisms and the like.

In spite of extensive research and developmental work carried out in the general field of endoscopic devices, no completely satisfactory binocular device of this type has heretofore been produced, all of the prior art mechanisms being objectionable in one or more major respects. It is, accordingly, a principal aim of the present invention to obviate the shortcomings of the prior art structures and to provide an improved, highly efficient and optically exact endoscopic viewing system which is practical in construction and which provides enhanced overall operability and utility.

It is an important feature of the invention that there is provided a unique optical system for an endoscope ensuring that a greater percentage of the image light rays reach the eyepiece for observation purposes.

Another important feature of the invention is that there is provided a viewing system which permits a full 360° about the optic viewing axis but retains the image in an upright disposition.

Still another important advantage of the novel optical system utilized in the endoscope of the invention is that it obviates any need to twist or otherwise to distort a fiber optical band or bundle.

A basic object of the invention is to provide binocular vision and stereoscopic viewing so that objects located in the field of view may be seen with both eyes to produce a visual image in three dimensions, thereby facilitating more accurate inspection of the field and object viewed.

The improved endoscope of the invention includes, in addition to a highly effective and reliable optical system, the more conventional auxiliary elements such as a surgical element and fluid flow passages. Additional useful elements which may conveniently be incorporated in the preferred embodiment of the invention include fluid pressure sensing and indicator means together with pressure regulator means and gauge means for monitoring and controlling the fluid flow rate and for adjusting and limiting the fluid pressure in the system.

In a preferred embodiment of the invention the optical system includes a dove prism for maintaining an erect or upright viewed image irrespective of rotation of the optical axis of the endoscopic optical system.

The improved endoscope of the invention constitutes an otpical viewing instrument which is more effective for exploring and inspecting interior and inaccessible cavities, such as the various body cavities, and may be used as a diagnostic and surgical instrument.

SUMMARY OF THE INVENTION

The enhanced utility of the endoscope of the present invention derives from its optical system which enables the user better to view and to examine body zones to be subjected to medical or surgical treatment. The instrument provides a field of view which includes more detail and structure than has heretofore been possible, all with the important added advantage of depth perception. The binocular arrangement of the instrument with its unique system for effectively rotating the objective element of the invention while maintaining the ocular lens and eyepiece in fixed position and while maintaining the image "vertical" provides viewing orientation never previously possible. That is, the rotation mechanism provides for a smooth, full 360° range of rotation with a rigid axial linkage, the image remaining upright to obviate any need for head rotation while viewing the object under inspection. Still another important feature of the invention is that the magnification of the image is variable as is also the depth of field.

Additional general important features of the invention are its superior throughput and enhanced resolution. Practical advantages of the invention are its high reliability and its relatively low cost to produce.

The above and other objects, features, utilities and advantages of the invention will be more clearly understood upon a review of the detailed description of the preferred embodiment considered with the drawings. The preferred embodiment is presented here only as an example and is not to be considered as limiting the invention in any way.

DESCRIPTION OF THE PREFERRED EMBODIMENT

In accordance with a preferred embodiment of the invention, the aims and objects are accomplished by providing an endoscope in which light from the same object is caused to pass through two parallel, substantially equivalent optical viewing paths delineated by an optical shaft which extends between the object viewed and the binocular viewing station. The light is collimated by objective lenses in each optical path and collimated light is then recollimated and focused by means of additional lens elements to produce real separate images at an image plane behind which there is mounted a special optical element consisting of a dove prism.

The optical assembly of the invention which includes a pair of juxtaposed long path lens systems utilizes linear linkage means which serve to ensure that when the optic shaft is rotated through a given angle, the viewed image remains fixed and upright in a secondary image plane. Finally, the separate images are deflected by additional optical elements to provide a magnified image which is ultimately viewed at a pair of eyepieces. The eyepieces provide binocularity, that is, depth perception in the image of the object viewed. An additional feature is means for illuminating the field of view and means for transmitting illuminating light from the light source to the field to be examined. Passages or conduit spaces are provided in the apparatus for the transmittal of irrigation fluid and for the manipulation of cauterization elements and surgical probes. The entire apparatus serves to ensure efficient, non-distorted image transmittal with extremely high resolution.

Referring more particularly to the drawing, there is shown in FIGS. 1,2,3,16 and 17, for the purposes of illustrative disclosure, a preferred embodiment of the binocular endoscope 20 of the invention.

Figure 1:
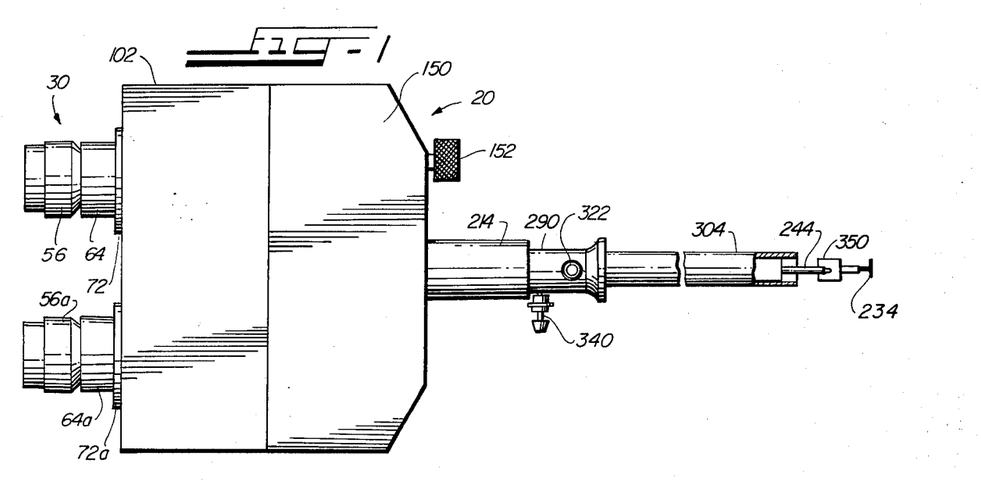
FIG. 1 is a top plan view of the binocular endoscope of the invention showing, generally, the physical orientation and arrangement of component elements.
Figure 2:
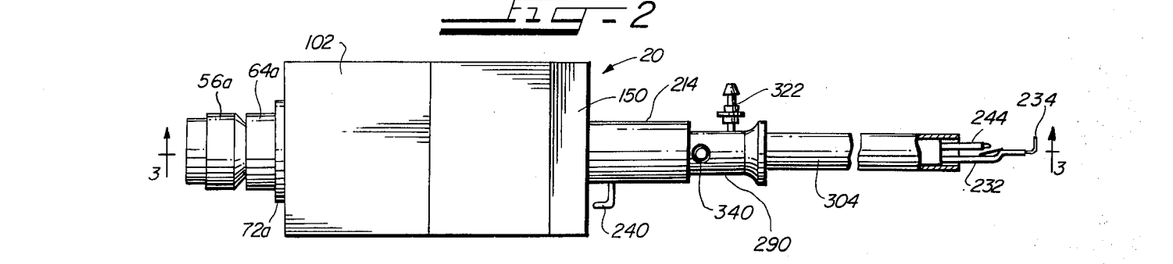
FIG. 2 is a side elevational view of the endoscope.
Figure 3:
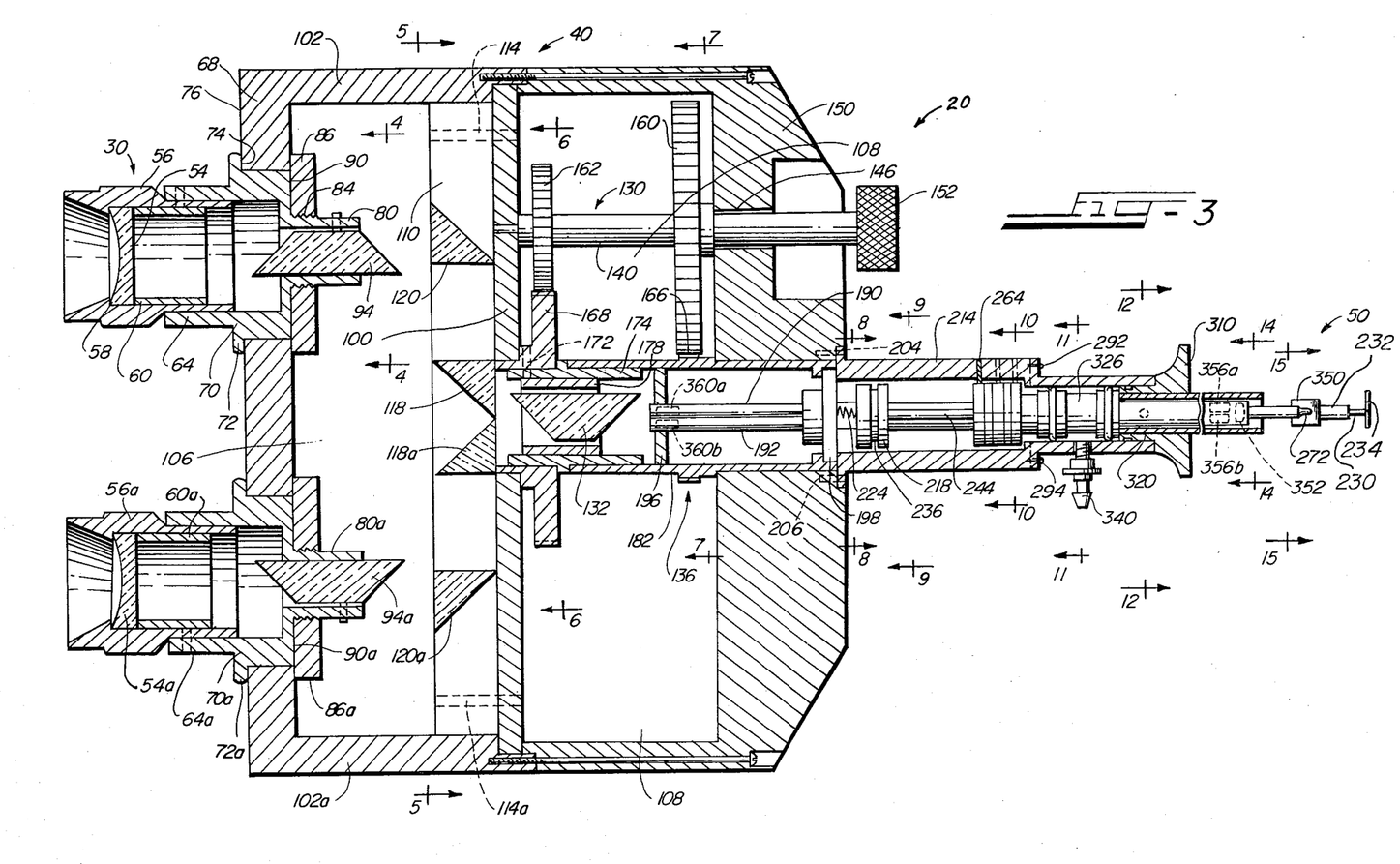
FIG. 3 is an enlarged longitudinal cross sectional view of the endoscope of the invention, taken substantially on the lines 3—3 of FIG. 2.
Figure 4:
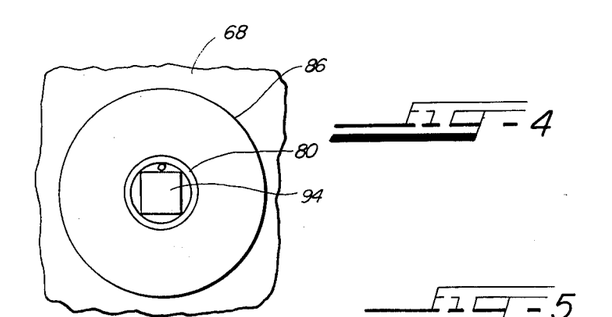
FIG. 4 is an elevational view looking reversely into the eyepiece assembly, and taken substantially on the lines 4—4 of FIG. 3.
Figure 5:
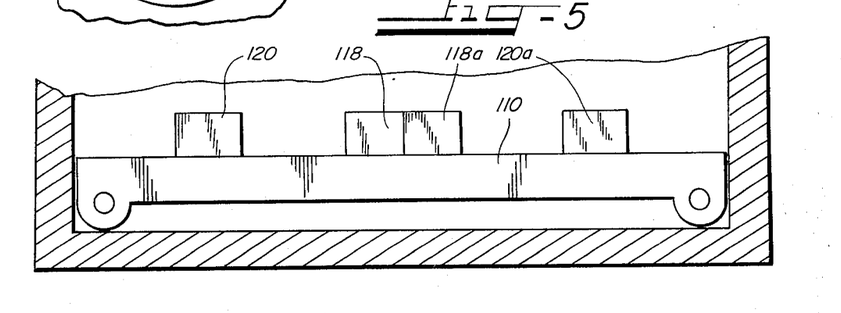
FIG. 5 is a transverse cross sectional view taken substantially on the lines 5—5 of FIG. 3.
Figure 6:
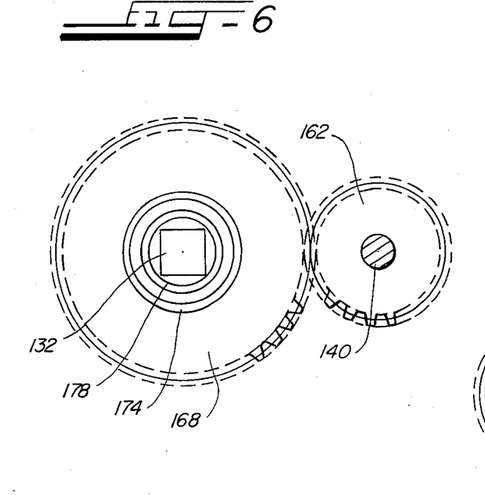
FIG. 6 is a view taken substantially on the lines 6—6 of FIG. 3 and showing the interengagement of two gear elements of the assembly for rotating the dove prism.
Figure 7:
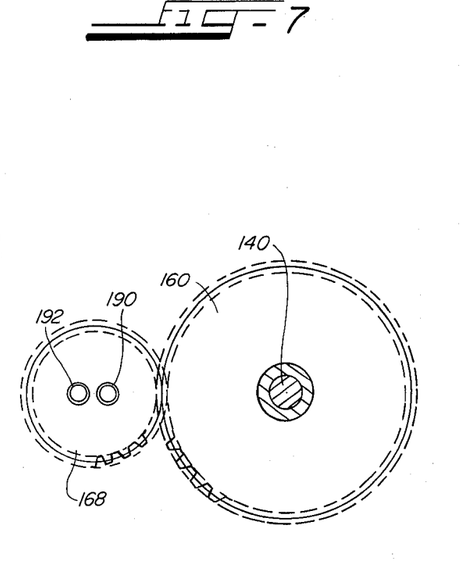
FIG. 7 is a cross sectional view taken substantially on the lines 7—7 of FIG. 3 and showing a second pair of gears involved in effecting the desired rotation and orientation of the dove prism.
Figure 8:
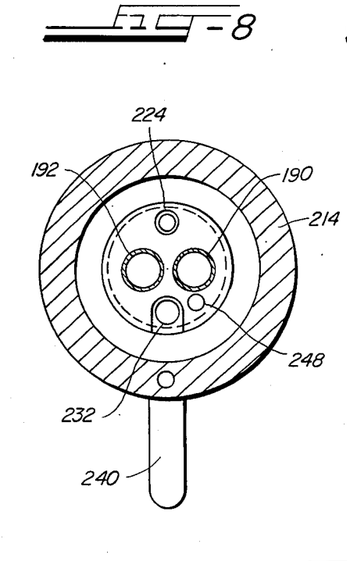
FIG. 8 is a transverse cross sectional view taken substantially on the lines 8—8 of FIG. 3.
Figure 9:
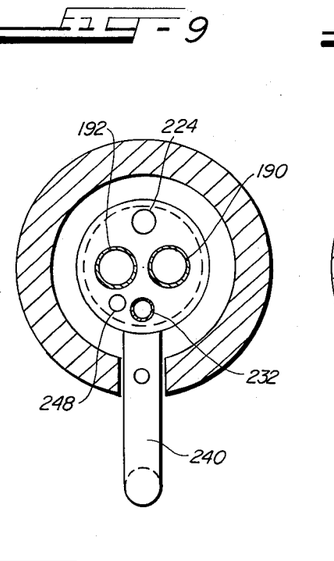
FIG. 9 is a transverse cross sectional view taken substantially on the lines 9—9 of FIG. 3.
Figure 10:
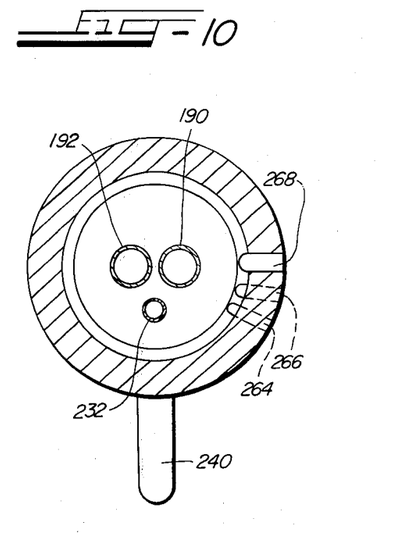
FIG. 10 is a transverse cross sectional view taken substantially on the lines 10—10 of FIG. 3.
Figure 11:
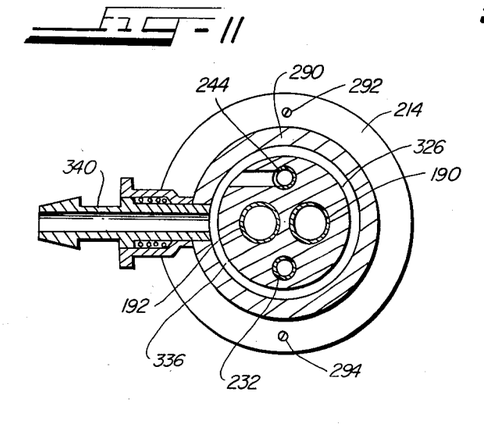
FIG. 11 is a transverse cross sectional view taken substantially on the lines 11—11 of FIG. 3.
Figure 12:
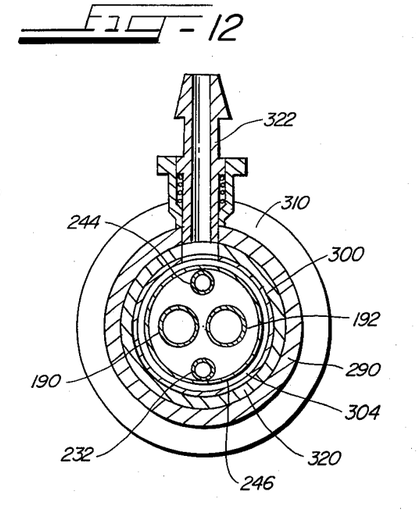
FIG. 12 is a transverse cross sectional view taken substantially on the lines 12—12 of FIG. 3.
Figure 13:
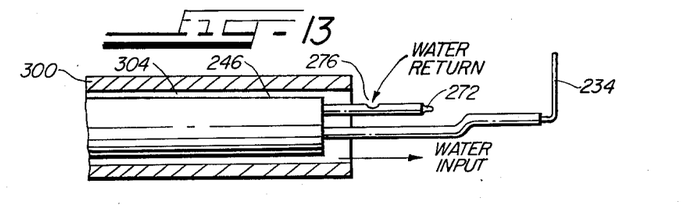
FIG. 13 is a fragmentary longitudinal cross sectional view taken substantially on the lines 13—13 of FIG. 3.
Figure 14:
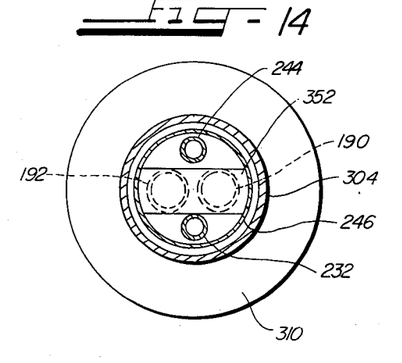
FIG. 14 is a cross sectional view taken substantially on the lines 14—14 of FIG. 3.
Figure 15:
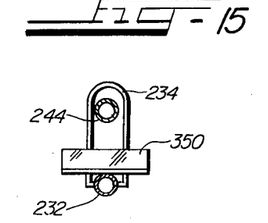
FIG. 15 is a cross sectional view taken substantially on the lines 15—15 of FIG. 3.

For convenience, the endoscope 20 is described herebelow as viewed in FIG. 3 from left to right. As shown, the device consists of several principal cooperating, interrelated functional components — an eyepiece assembly 30, a main housing 40, and a probe assembly 50. The optics structure is essentially bilaterally symmetrical about a longitudinal plane or with reference to an optical axis. Accordingly, one "half" of the instrument is described in detail, the other half being designated by the same numbers, but with an added "a."

Each eyepiece assembly 30 of the binocular endoscope includes an ocular lens 54, each lens being secured in an eyepiece housing or tubing section 56 against an end flange 58 by means of an internal sleeve or bushing 60. The lens-carrying tube section 56 is freely rotatable in an enveloping cylindrical ocular tube 64, the forwardly directed end of which is generally T-shaped in cross section. The ocular tube 64 projects through and seats within a cooperating opening in a rear end wall 68 of the main housing 40. While the particular mode of securing the ocular tube 64 is not critical, in the specific embodiment of the apparatus shown an enlarged ring portion 70 of the ocular tube 64 is formed with an integral, annular, radially outwardly directed flange 72 having a lateral face 74 which abuts the outer surface 76 of the main housing end wall 68 as a stop. A forwardly extending, reduced diameter cylindrical sleeve 80 of the ocular tube 64 is formed with external threads 84, and a cooperating threaded retaining ring 86 is mounted on the sleeve 80 to seat against an inner face 90 of the main housing end wall 68 thereby to lock the eyepiece assembly 30 in place.

A lens 94 in the form of a dove prism is secured in the sleeve 80. In the arrangement described, the eyepiece housing 56 and the dove prism 94 can rotate freely about their common axis. An internal dividing wall 100 spans the main housing 40 between opposed side walls 102, 102a thereof to divide the main housing into two chambers 106 and 108, and a bracket 110 bolted 114,114a to the wall 100 carries deflection prisms 118,120 (and 118a and 120a), all supported within the rearward cavity or chamber 106.

The forward cavity 108 of the main housing 40 contains a gear train 130 for rotating a principal dove prism 132 with reference to a coaxial main shaft assembly 136. As shown in FIG. 3, a gear support shaft 140 is journaled 144 at one end in the dividing wall 100 and at the other end 146 in the main housing forward end wall 150, the shaft 140 terminating externally of the housing 40 in a knurled knob 152. Secured to the shaft 140 for rotation therewith are two Boston type gears 160 and 162 coupled respectively to a pair of forward and rearward ring gears 166 and 168 which drive, respectively, the main shaft assembly 136 and the dove prism 132. The rearward ring gear 168 is attached to or fixedly locked 172with a main dove prism housing or ring 174, and the latter is secured to a coaxial inner sleeve 178 in which the main dove prism 132 is mounted so that rotation of the gear shaft 140 (by means of the knurled knob 152) and the gear 162 carried thereon causes rotation of the intercoupled gear 168 and the attached internal sleeves to rotate the dove prism 132.

The forward ring gear 166 is carried by and secured to an optical shaft casing sleeve 182 journaled in the forward end wall 150 of the housing 40 for rotation coaxially with the dove prism ring 174. The gear combinations 162, 168 and 160,166 are of such diameters (gears 162 and 166 have radius R and gears 160 and 168, radius 2R) that upon rotation of the optic shaft gear 166 and its associated sleeve 182 through an angle $\phi$. The dove prism drive gear 168 is rotated through an angle $\phi/2$ in the same angular direction. The arrangement described makes it possible, in accordance with the action of the dove prism 132, to maintain the viewed image upright while the objective lens system is rotated to provide a full 360° C of selectable viewing field.

Referring further to FIG. 3, and to FIGS. 8–10, 16 and 17 the optical system of the invention includes a pair of lens support tubes or lens housing tubes 190, 192 positioned within the optical sleeve 182 to extend parallel to and symmetrically disposed with respect to the optical axis of the device. Two longitudinally spaced rear and forward plates 196, 198 provide stabilizing support.

Fastened 204,206 to the front face 210 of the main housing 40 and extending forwardly thereof is a thrust bushing and slip ring casing 214. A thrust bushing 218 slidably supported within the casing 214 is biased forwardly by a spring 224 interposed between the forward face 226 of the forward lens support plate 198 and the rear face 228 of the bushing 218.

The endoscope of the invention is provided with a cauterizing loop or surgical element consisting of an excising wire 230 encased in a thin-walled pipe 232 and terminating at its forward end in a loop 234. The wire 230 projects forwardly of the thrust bushing 218 and is fastened thereto for movement therewith. The wire itself is connected to an electrical jack whereby electrical current may be plugged in and fed to the loop 234.

The thrust bushing 218 is formed with an annular groove 236 into which one end of a slide rail 238 supported finger lever 240 (FIG. 17) projects, the lever extending exteriorly of the casing 214 through an elongated slide slot 242. By manually shifting the trigger 240 and the thrust bushing 218 the attached wire 230 and loop 234 assembly may be urged rearwardly against the pressure of the spring 224 to provide controlled forward and rearward manipulation of the surgical loop 234.

Enveloping the lens support tubes 190,192, a pipe guide 244 for the light illuminating wires, and the sheath 232 encasing the excising wire 230 is a thin inner sleeve or casing 246 preferably of stainless steel.

In the embodiment of the invention shown, the thrust bushing 218 rides on a guide rod 248, the latter being connected electrically to the excising wire 230 by means of a slide contractor carried by the thrust bushing 218. An insulated slip ring assembly 252 located forwardly of the thrust bushing 218 in the casing 214 is ringed with three longitudinally spaced conducting hands 256,258 and 260 and the circumscribing casing wall 214 is formed with corresponding in-line radial access bores 264, 266, 268 for accommodating band contacting probes (not shown). Two probe and band combinations (bands 258 and 260) deliver electrical power (from a source not shown) to an illuminating bulb 272, and the third probe and band (256) supply power to the wire loop 234.

Figures 16, 17:
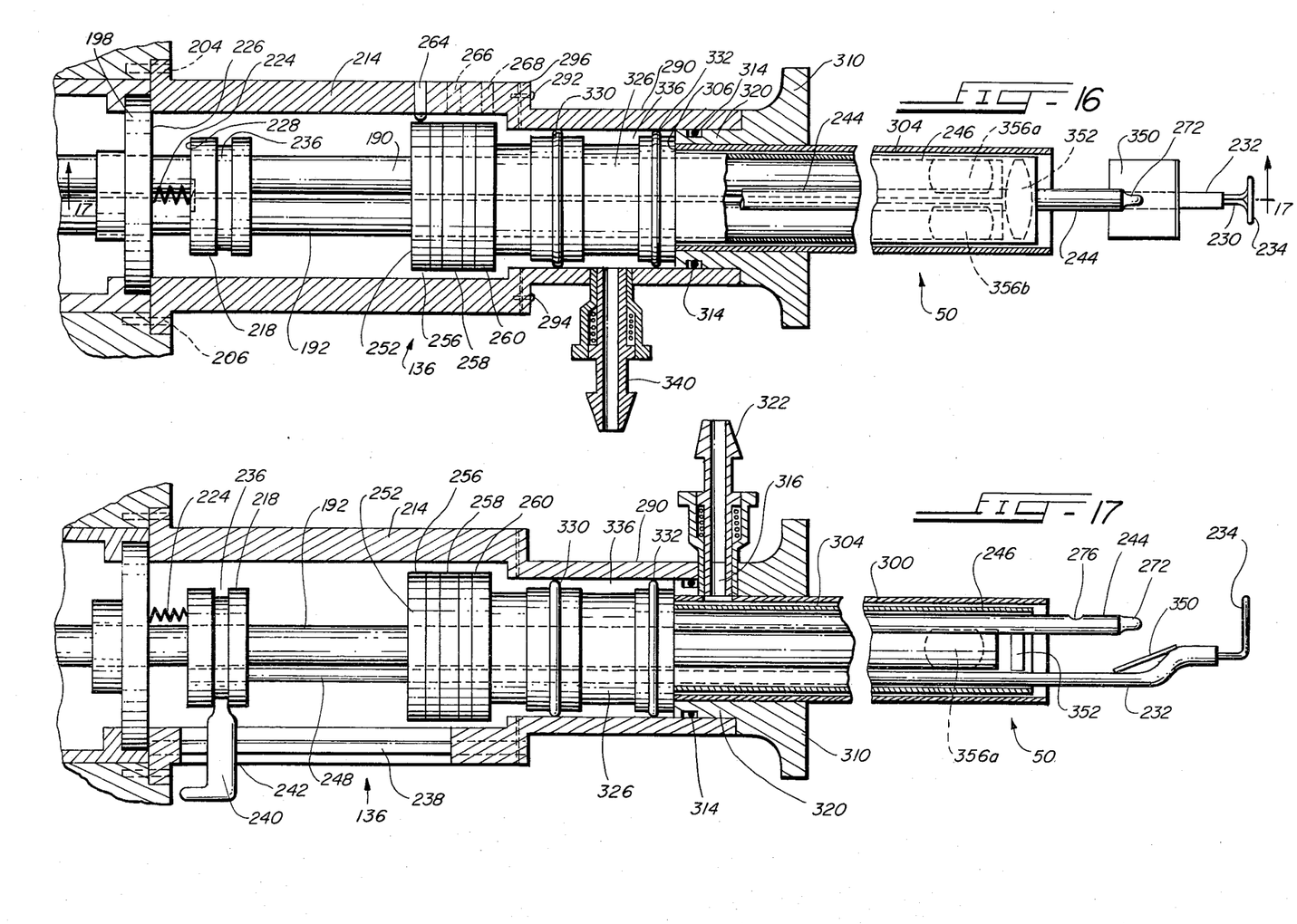
FIG. 16 is an enlarged longitudinal cross sectional view of the forward portion of the apparatus shown in FIG. 3.
FIG. 17 is a longitudinal cross sectional view taken substantially on the lines 17—17 of FIG. 6.

As indicated in FIGS. 16 and 17 a tubular housing 290 coaxial with the slip ring casing 214 is fastened 292,294 at an integral flange 296 to the forward annular end face of the slip ring casing 214.

The binocular endoscope is provided with a fluid flow system including water or isotonic fluid input and discharge conduits. Enveloping the inner steel sleeve 246 is an outer plastic sleeve 300 whose inner diameter is somewhat larger than the outer diameter of the internal sleeve 246 so that an annular passage 304 is defined between the coaxial tubes 246 and 300. The rearward end 306 of the outer sheath 300 is sealed or otherwise sleeved within a surrounding annular flanged collar 310, and the latter is in turn telescoped within the tubular housing 290, a fluid-tight seal being provided by an O-ring 314.

Water or isotonic fluid may be introduced into the device through a radial passage or bore 316 (FIG. 17) extending through the housing 290, the stub annular wall 320 of the collar 310, and through the outer sheath 300 to provide a duct communicating with the annular passage 304, the latter being open at its forward, fluid-delivery end. An external stub pipe connector 322 to which a hose (not shown) may be attached is fastened at the port of the housing 290 to complete a fluid inflow route from the exterior of the device to a treatment zone into which the probe portion 50 of the endoscope may be inserted.

Fluid discharge or exhaust is through the same tube 244 which houses the electrical leads to the light 272, the wall of the tube 244 being formed, near a forward end thereof, with a hole 276. In a zone between its forward end and its end supported within the slip ring assembly 252, the conduit 244 passes through a spool-like spindle 326 disposed within the housing 290. A pair of axially spaced spindle-encircling O-rings 330,332 seal between the spindle 326 and the housing 290 to define an annular cavity or zone 336. The spindle is drilled radially in this zone 336 to establish fluid communication between the zone 336 and the adjacent end opening 276 of the conduit 244. Finally, the wall of the housing 290 drilled through opposite the zone 336 and the drill port is fitted with a stub pipe connector 340 to complete the water or isotonic fluid discharge circuit.

It will be appreciated by those skilled in the art that precise optical orientation and alignment of all component parts in the optical system are essential in ensuring optimum operation. While several possible techniques may be utilized in mounting the principal dove prism 132, in accordance with the present invention the following technique has proven particularly useful.

As a first step, the prism 132 is oriented optically by means of a laser so that the prism rotates properly about its own axis. Having been fixed in the established orientation, the outer perimeter of the prism is ground onto a circular cross section or into a partial circular cross section so that the axis of the prism will be concentric with and parallel to the axis of the inner prism mounting sleeve 178. The prism is then slipfitted into the sleeve 178 in which the prism is held frictionally. Finally, the prism mounting sleeve with the prism in place is located in the prism housing ring 174.

The optical system is so designed that only quasi-parallel light passes through the dove prisms 132 and 94 and 94a of the device.

In view of the foregoing description, the optics of the apparatus will be readily understood. The arrangement and placement of the optics elements described are such as to provide binocularity, that is, depth perception of the image of the object viewed. A tilted front-mounted mirror 350 directs the image of a light illuminated object or field through a front lens element 352 and then through each of a pair of tube-mounted lens elements 356a, 360a and 356b, 360b, through the dove prism 132, the deflection prisms 118,120 and the eyepiece assembly 30.

Among the important benefits achieved in accordance with the practice of the invention and made possibly by the structure described are full viewing through 360° of rotation, non-distorted image transfer with high resolution achieved through the long path lenses, binocularity or depth perception of the image of the object viewed, maintenance of the image fixed and upright as viewed, and controlled magnification and focusing. The apparatus provides selectable field viewing through any desired angle.

While disclosures of preferred embodiments of the apparatus of the invention have been provided, it will be apparent that numerous modifications and variations thereof may be made without departing from underlying principles of the invention.

For example, the long path lens means may include optic tubes which define compartments extending axially between the forward and rear lenses. These compartments may be filled with a high optical index immersion oil, and sealed with O-rings so that the combination of the lenses with the intermediate oil column produces, in effect, in each optic tube 190 and 192, a long path length lens. Alternatively, the light transmission means may consist of a fiber optics system including a bundle of closely grouped elongated light-guiding fibers extending lengthwise within an annular passage between elongated, coaxial inner and outer tubes of the endoscope apparatus. An illuminable bulb located at a rearward end of the light-guiding fibers, in the arrangement described, delivers light to the fibers for transmittal to a forward zone of examination and treatment.

What is claimed is:

1. A binocular endoscope for obtaining three dimensional visual perception of an image of an object to be viewed,
said endoscope comprising:
a pair of elongated, coextensive, juxtaposed optical systems for directing and guiding object-reflected light simultaneously through two paralleling substantially equivalent optical viewing paths delineated by an optic shaft extending between the object viewed and a binocular viewing station,
said optical systems including
long path length lens means including means for focusing the image for viewing at the viewing station,
light path directing means operative to establish a parallax angle between the two viewing paths thereby to provide depth perception of the image of the object viewed,
ocular means for receiving and perceiving an image optically transmitted from the viewed object to the viewing station,
optic shaft means and means for rotatably shifting said optic shaft means relative to said ocular means of the endoscope to facilitate and effectuate continuously variable full-field viewing of an object to be examined, and
shift compensating optic means for maintaining an image of the object viewed in a disposition which is fixed as to angular spatial orientation relative to the viewing station irrespective of manipulative rotation of the optic shaft of the endoscope for selected field viewing.

2. The structure as set forth in claim 1 and further comprising a generally tubular inner tube constituting an enveloping sheath for components of said optical systems.

3. The structure as set forth in claim 2 and further comprising an outer tube substantially coaxial with said inner tube therewithin to form an elongated annular passage therebetween.

4. The structure as set forth in claim 3 and further comprising a light source and light transmission means for delivery of light energy from said light source to impinge upon an object to be illuminated for viewing.

5. The structure as set forth in claim 4 wherein said light transmission means consists essentially of a fiber optics system including a bundle of closely grouped elongated light guiding fibers extending lengthwise in said annular passage between said outer and said inner tube.

6. The structure as set forth in claim 5 wherein said light source includes an illuminable bulb adjacent a a rearward end of said light-guiding fibers for delivery of light to said fibers for transmittal thereby to a forward zone of examination and treatment.

7. The structure as set forth in claim 3 and further comprising passage means extending through said inner tube along the length thereof, said passage means adapted to serve as a conduit for irrigation and treating fluids directed into and from a zone of examination and treatment adjacent a forward terminus of said endoscope.

8. The structure as set forth in claim 1 and further comprising light source means carried by said endoscope for illuminating an object to be viewed.

9. The structure as set forth in claim 8 and further comprising slip ring means for completing electrical connections between said light source means and external electrical power supply.

10. The structure as set forth in claim 1 wherein said shift-compensating optic means includes a dove prism.

11. The structure as set forth in claim 10 and further comprising an inner housing shaft,
means fastening said dove prism coaxially to said inner housing shaft for rotation therewith,
an optic shaft,
lever means,
means connecting said lever means to said optic shaft for effecting rotation thereof,
linkage means intercoupling said optic shaft with said dove prism to effect rotation of said dove prism by an angle of $+ \phi/2°$ upon rotation of said optic shaft through an angle of $+\phi°$,
thereby to maintain the image of the object viewed fixed and upright with reference to an image appearing at the viewing station.

12. The structure as set forth in claim 1 and further comprising outer housing means, said outer housing means constituting support means for said ocular means carried thereby, and
wherein said means for rotatably shifting said optic shaft means includes gear means functionally interposed between said optic shaft means and said outer housing means, whereby said optic shaft means is rotatable while said ocular means is held firmly fixed in position.

13. The structure as set forth in claim 12 and further comprising hand-actuable position lever means connected to for rotation of said optic shaft means and said gear means coupled thereto, thereby to select and to change a field of viewing.

14. The structure as set forth in claim 12, and further comprising inner housing shaft means rotatably supported coaxially within said housing means, and wherein said gear means intercouple said inner housing shaft means with said optic shaft means,
said gear means comprising, in combination, an optic shaft ring gear of radius R, an inner housing shaft ring gear of radius 2R coaxial therewith, and a pair of shaft-mounted intercoupling gears having radii of 2R and R and meshing respectively with said optic shaft gear and said inner housing shaft gears, whereby rotation of said optic shaft gear through an angle $+\phi$ effects a rotation of said inner housing shaft gear through an angle of $+\phi/2$.

15. The structure as set forth in claim 12 wherein said gear means includes means for full 360° rotation of said optic axis shaft with respect to said outer housing means.

16. The structure as set forth in claim 1 and further comprising mirror means in said optical systems, said mirror means being oriented so as to receive, at different angles for each of said optical systems, light reflected from an object to be viewed, thereby to establish parallax viewing, said mirror means being titled at a slight angle with respect to a center axis of rotation of said optical systems.

17. The structure as set forth in claim 1 and further comprising a pair of elongated hollow optic tubes in side-by-side relation in said endoscope, a plurality of lens elements disposed within each of said tubes and extending transversely thereof and being linearly spaced therewithin, said lens elements serving to collimate object-reflected light and to focus and to produce images of the viewed object at an image plane in each of said optical systems.

18. The structure as set forth in claim 17 and further comprising a light transmitting medium of a high optical index disposed within each of said optic tubes between said lens elements contained therein.

19. The structure as set forth in claim 18 wherein said light transmitting medium is a high optical index fluid, and further comprising seal means to preclude escape of said fluid from within said tubes.

20. The structure as set forth in claim 1 wherein said light path directing means includes object-reflected light collection lens means disposed in said optical systems, thereby to establish, in conjunction with said long path length lens means a parallax angle between said viewing paths to provide depth perception in the image of the object viewed.

21. The structure as set forth in claim 20 and further comprising mirror means and means supporting said mirror means forwardly of said light collection lens means, said mirror means being tilted at a slight angle to an axis of rotation of the optic axis.

22. The structure as set forth in claim 1 and further comprising tissue treatment means, and means for controlled manipulation of said tissue treatment means in carrying out a surgical technique in a zone of treatment into which said endoscope is introduced.

23. The structure as set forth in claim 22 and further comprising slip ring means for completing electrical connections between said tissue treatment means and an external electrical power supply.

24. The structure as set forth in claim 1 wherein said shift compensating optic means includes a single dove prism, interposed in and operable in the two paralleling optical viewing paths of said juxtaposed optical systems.

25. In a binocular endoscope, the method of providing angularly spatially oriented, full-field viewing of an object to be examined, and three dimensional visual perception of an image of the object examined, said method comprising the steps of:

supporting a pair of elongated optical systems in a coextensive, juxtaposed disposition to define an optic shaft and to direct and guide object-reflected light simultaneously through two paralleling, substantially equivalent optical viewing paths symmetrical with respect to an optic shaft extending between the object viewed and binocular viewing station, illuminating the object to be examined, interposing light path directing means forwardly of said pair of optical systems and between said optical systems and the object to be viewed, thereby to establish a parallax angle between the two viewing paths and to provide depth perception of the image of an object viewed, mounting ocular means at corresponding functional positions at an end of each of said pair of optical systems remote from the object to be viewed, thereby to receive and to perceive an image optically transmitted from the viewed object to the viewing station, rotatably shifting said optic shaft relative to said ocular means to provide continuously variable full-field viewing of an object to be examined, and intercoupling shift compensating optic means between said optic shaft and said ocular means to maintain an object viewed in a disposition which is fixed as to angular spatial orientation relative to the viewing station irrespective of manipulative rotation of the optic shaft of the endoscope for selected field viewing.

* * * * *